United States Patent
Justin

(10) Patent No.: US 6,527,777 B2
(45) Date of Patent: *Mar. 4, 2003

(54) DEVICE FOR REPAIRING A SOFT-TISSUE TEAR AND METHOD

(75) Inventor: Daniel F. Justin, Logan, UT (US)

(73) Assignee: Ethicon, Inc., Somerville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/805,495

(22) Filed: Mar. 13, 2001

(65) Prior Publication Data

US 2001/0037113 A1 Nov. 1, 2001

Related U.S. Application Data

(63) Continuation-in-part of application No. 09/542,100, filed on Apr. 4, 2000.

(51) Int. Cl.⁷ ................................................ A61B 17/56
(52) U.S. Cl. ........................... 606/73; 606/75; 606/65; 606/72; 411/310; 411/415
(58) Field of Search ............................... 606/60, 65, 72, 606/73, 76, 77, 86, 96, 98, 99, 104, 213, 216, 218; 411/263, 310, 395, 413, 415

(56) References Cited

U.S. PATENT DOCUMENTS

| 65,651 A | 6/1867 | Davies |
|---|---|---|
| 146,023 A | 12/1873 | Russell |
| 197,467 A | 11/1877 | Harvey |

(List continued on next page.)

FOREIGN PATENT DOCUMENTS

| CA | 731381 | 4/1966 |
|---|---|---|
| CA | 1007493 | 3/1977 |
| DE | 2618344 | 8/1977 |
| DE | 3215228 | 11/1983 |
| DE | 3630863 A1 | 3/1988 |
| DE | 4021550 | 1/1991 |
| EP | 0172130 | 2/1986 |
| EP | 0544868 | 6/1992 |
| FR | 2588332 | 4/1987 |
| GB | 598834 | 2/1948 |
| IT | 365613 | 12/1938 |
| JP | 45-24729 | 8/1964 |
| SU | 77837 | 6/1918 |
| SU | 1216-466 A | 3/1986 |
| WO | 89/09030 | 10/1989 |
| WO | 90/02526 | 3/1990 |
| WO | WO 91/09572 | 7/1991 |
| WO | 93/00518 | 1/1993 |
| WO | 94/16636 | 8/1994 |
| WO | WO 95/15727 | 6/1995 |

OTHER PUBLICATIONS

Herbert, "Bone Screws for Small Bone Fractures," *Zimmer*, 97–1152–01, 1992, pp. 1–14.

*Primary Examiner*—Pedro Philogene
(74) *Attorney, Agent, or Firm*—Allen, Dyer, Doppelt, Milbrath & Gilchrist, P.A.

(57) ABSTRACT

A fastener, driving device, and method are provided for repairing a tear in soft tissue of a patient, such as a meniscal tear in a knee. The fastener has a distal section having a narrowing cross section toward the distal end and a helical protrusion along a central section between the proximal end and the distal end. Along a distal section extending from the distal end, the helical pitch is substantially constant; along a central section between the distal section and the proximal end, the helical pitch decreases from the distal end to the proximal end. The substantially constant pitch along the distal section assists in preventing a stripping of the helical section. At the proximal end is a head having a diameter greater than a major root diameter of the central section. The head is for improving the tissue retention characteristics of the fastener.

14 Claims, 3 Drawing Sheets

U.S. PATENT DOCUMENTS

| | | | |
|---|---|---|---|
| 197,933 A | 12/1877 | Harvey | |
| 1,980,093 A | 11/1934 | Rosenberg | |
| 2,165,149 A | 7/1939 | Olson | |
| 2,263,137 A | 11/1941 | Oestereicher | |
| 2,356,098 A | 8/1944 | Steinle et al. | |
| 2,377,405 A | 6/1945 | Davies | |
| 2,382,019 A | 8/1945 | Miller | |
| 2,383,231 A | 8/1945 | Anderton | |
| 2,419,555 A * | 4/1947 | Fator | 411/415 |
| 2,633,091 A | 3/1953 | Wenger et al. | |
| 2,801,631 A | 8/1957 | Charnley | |
| 2,842,180 A | 7/1958 | Brown et al. | |
| 3,051,169 A | 8/1962 | Grath | |
| 3,079,181 A | 2/1963 | Van Der Wissel | |
| 3,124,408 A * | 3/1964 | Oestereicher | 411/310 |
| 3,233,500 A | 2/1966 | De Vellier | |
| 3,454,070 A * | 7/1969 | Phipard, Jr. | 411/310 |
| 3,664,540 A | 5/1972 | Witkin | |
| 3,799,229 A | 3/1974 | Johnson | |
| 3,861,269 A | 1/1975 | Laverty | |
| 3,915,162 A | 10/1975 | Miller | |
| 4,027,573 A | 6/1977 | Laverty | |
| 4,058,856 A | 11/1977 | Doerre et al. | |
| 4,059,102 A | 11/1977 | Devas | |
| 4,069,980 A | 1/1978 | Yarem et al. | |
| 4,175,555 A | 11/1979 | Herbert | |
| 4,340,184 A | 7/1982 | Poss | |
| 4,456,005 A | 6/1984 | Lichty | |
| 4,463,753 A | 8/1984 | Gustilo | |
| 4,468,200 A | 8/1984 | Münch | |
| 4,537,185 A | 8/1985 | Stednitz | |
| 4,640,271 A | 2/1987 | Lower | |
| 4,723,541 A | 2/1988 | Reese | |
| 4,842,464 A | 6/1989 | Green | |
| 4,844,676 A | 7/1989 | Adamek | |
| 4,854,311 A | 8/1989 | Steffee | |
| 4,863,383 A | 9/1989 | Grafelmann | |
| 4,873,976 A | 10/1989 | Schreiber | |
| 4,884,572 A | 12/1989 | Bays et al. | |
| 4,892,429 A | 1/1990 | Giannuzzi | |
| 4,895,148 A | 1/1990 | Bays et al. | |
| 4,917,554 A | 4/1990 | Bronn | |
| 4,940,467 A | 7/1990 | Tronzo | |
| 4,950,270 A | 8/1990 | Bowman et al. | |
| 4,959,064 A | 9/1990 | Engelhardt | |
| 5,019,078 A | 5/1991 | Perren et al. | |
| 5,019,079 A | 5/1991 | Ross | |
| 5,042,982 A | 8/1991 | Harms et al. | |
| 5,059,206 A * | 10/1991 | Winters | 606/213 |
| 5,085,660 A | 2/1992 | Lin | |
| 5,120,171 A | 6/1992 | Lasner | |
| 5,147,363 A | 9/1992 | Härle | |
| 5,152,790 A | 10/1992 | Rosenberg et al. | |
| 5,169,400 A | 12/1992 | Mühling et al. | |
| 5,180,382 A | 1/1993 | Frigg et al. | |
| 5,190,426 A | 3/1993 | Wieder et al. | |
| 5,226,766 A | 7/1993 | Lasner | |
| 5,246,441 A | 9/1993 | Ross et al. | |
| 5,252,016 A | 10/1993 | Schmid et al. | |
| 5,259,398 A | 11/1993 | Vrespa | |
| 5,300,076 A | 4/1994 | Leriche | |
| 5,306,275 A | 4/1994 | Bryan | |
| RE34,871 E | 3/1995 | McGuire et al. | |
| D356,868 S | 3/1995 | Broberg et al. | |
| 5,403,136 A * | 4/1995 | Mathys | 606/73 |
| 5,470,334 A | 11/1995 | Ross et al. | |
| 5,484,440 A | 1/1996 | Allard | |
| 5,492,442 A | 2/1996 | Lasner | |
| 5,536,127 A | 7/1996 | Pennig | |
| 5,562,672 A | 10/1996 | Huebner et al. | |
| 5,562,704 A | 10/1996 | Tamminmäki et al. | |
| 5,569,252 A | 10/1996 | Justin et al. | |
| 5,569,264 A | 10/1996 | Tamminmaki et al. | |
| 5,571,139 A | 11/1996 | Jenkins, Jr. | |
| 5,730,744 A | 3/1998 | Justin et al. | |
| 5,743,912 A | 4/1998 | Lahille et al. | |
| 5,779,704 A | 7/1998 | Kim | |
| 5,871,486 A | 2/1999 | Huebner et al. | |
| 5,964,768 A * | 10/1999 | Huebner | 606/73 |
| 6,030,162 A * | 2/2000 | Huebner | 411/310 |

* cited by examiner

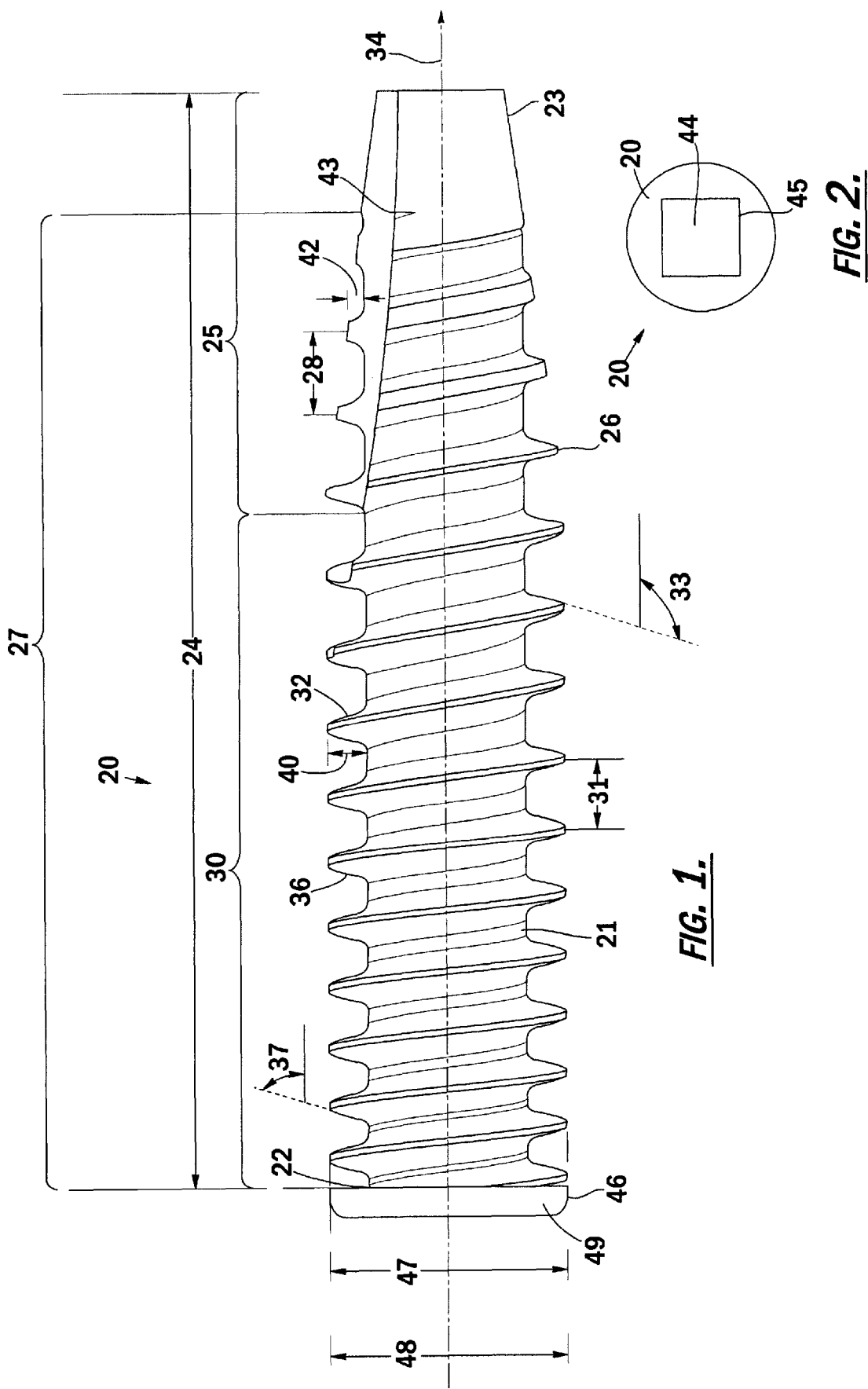

DEVICE FOR REPAIRING A SOFT-TISSUE TEAR AND METHOD

CROSS-REFERENCE TO RELATED APPLICATIONS

This application is a continuation-in-part of and incorporates by reference co-pending application Ser. No. 09/542,100, filed Apr. 4, 2000, commonly owned with the present application.

BACKGROUND OF THE INVENTION

1. Field of the Invention

The present invention relates to surgical devices and methods for repairing tissue tears and, more particularly, to a device and method for repairing a soft-tissue tear in a knee.

2. Description of Related Art

The repair of soft tissue tears represents a persistent problem in orthopedic practice. It is known to apply sutures and various types of fixation devices to such tears.

Among the soft tissue sites that require fixation are the menisci of the knee. The material of the menisci is collagenous, and the fibers are oriented generally circumferentially. Posterior peripheral tears of the menisci may be treated by an open technique, wherein sutures are placed along the tear. An arthroscopic technique may also comprise placing sutures along the tear, but in this method through a cannula.

There are a number of fastener-type devices that are known in the art: Screiber (U.S. Pat. No. 4,873,976); Bays et al. (U.S. Pat. Nos. 4,884,572 and 4,895,148); Winters (U.S. Pat. No. 5,059,206); and Justin and Winters (U.S. Pat. Nos. 5,503,634 and 5,730,744). Bone screws are disclosed by Huebner et al. (U.S. Pat. Nos. 5,562,672 and 5,871,486).

SUMMARY OF THE INVENTION

It is an object of the present invention to provide a fastener, delivery device, and method for repairing a tear in soft tissue.

It is a further object to provide such a fastener that is made from a nontoxic, biocompatible, bioabsorbable plastic specially designed to maintain its structural integrity during the healing of the tear and to prevent tissue abrasion.

It is an additional object to provide such a fastener having a shape designed to compress the tear.

It is another object to provide such a fastener shaped to resist forces tending to pull apart the meniscal tear during healing.

It is also an object to provide such a fastener that resists stripping and has superior tissue retention characteristics.

These and other objects are attained with the fastener and delivery device system and method of the present invention, a fastener designed for repairing a tear in soft tissue of a patient, a particular exemplary embodiment comprising a meniscal tear in a knee, although this is not intended as a limitation. The fastener has a proximal end, a distal end, and a distal section having a narrowing cross section toward the distal end. In use an insertion of the fastener into soft tissue is facilitated by this narrowed distal end, which takes the form in a preferred embodiment of a generally conical-shaped distal tip.

The fastener further has a helical protrusion along a central section between the proximal end and the distal end. Along a distal section extending from the distal end, the helical pitch is substantially constant; along a central section between the distal section and the proximal end, the helical pitch decreases from the distal end to the proximal end. In use the decrease in the helical pitch along the central section can serve to bring two sides of the tear into apposition as the fastener is advanced across the two sides of the tear in a screwing motion. The substantially constant pitch along the distal section assists in preventing a stripping of the helical section.

At the proximal end is a head having a diameter greater than a major root diameter of the central section. The head is for improving the tissue retention characteristics of the fastener.

In an alternate embodiment of the fastener, the variable-pitch helical protrusion has means for resisting an axial force from pulling the fastener out of the tear and from pulling the two sides of the tear apart. Specifically, the resisting means comprises the helical protrusion having a buttress form.

In a preferred embodiment, the fastener material comprises a biodegradable plastic biocompatible with the soft tissue of the patient. The material is specifically designed to be biodegradable within a first time span greater than or equal to a second time span over which the sides of the tear can knit together. This feature permits the fastener to remain in place for as long as required for the tear to heal, but ultimately to biodegrade and be dissipated harmlessly into the patient's system.

The material is further designed to have elastomeric properties compliant with those of the meniscus in order to confer biofunctionality.

A further feature of the present invention comprises a delivery device for introducing the above-described fastener into the area of the patient's soft tissue to be repaired. A feature of the fastener permitting a mating with a delivery device comprises the fastener's having an axial bore extending along the helical axis proceeding from the proximal end. The bore preferably has a noncircular cross-sectional shape so that an elongated driving device having a noncircular cross-sectional shape and dimensioned to pass into the bore can enter the bore and turn the screw. The fastener can then be advanced into the soft tissue by being rotated by the driving device in a direction having a handedness commensurate with the helically shaped protrusion. Simply put, the fastener appears as a variable-pitch screw that is internally drivable by rotation of an elongated member inserted into its bore.

The elongated driving device of the present invention for driving the fastener as described above has a distal end having means for mating with the fastener proximal end, and a proximal end having means for being rotationally driven. In use the fastener is mated with the driving device distal end, the fastener and distal end of the driving device are positioned adjacent the tear, and the means for being driven is rotated in a direction having a handedness commensurate with the helically shaped protrusion, thereby advancing the fastener across the tear.

In a specific embodiment of the system, the driving device further has a noncircular cross-sectional shape along a distal section adjacent the distal end. The fastener bore as described above has a noncircular cross-sectional shape dimensioned to permit the distal section of the driving device to pass into the bore and to permit relative axial sliding and rotational coupling movement therebetween. The axial slidability permits the driving device to be mated by sliding the driving device distal section into the fastener bore and to be removed once the tear has been breached by sliding the driving device out of the bore.

The method of the present invention is for repairing a tear in soft tissue of a patient. The method comprises the steps of providing a fastener having the features as described above. The fastener is then inserted into an area of soft tissue adjacent the tear. The distal end of the fastener is manipulated to a position generally normal to a long axis of the tear, and the fastener is driven across the tear in a screwing motion. The decrease in the helical pitch serves to bring two sides of the tear into apposition as the fastener is advanced.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view of the fastener of the present invention.

FIG. 2 shows the fastener in cross section.

DETAILED DESCRIPTION OF THE PREFERRED EMBODIMENTS

Figure 3A:
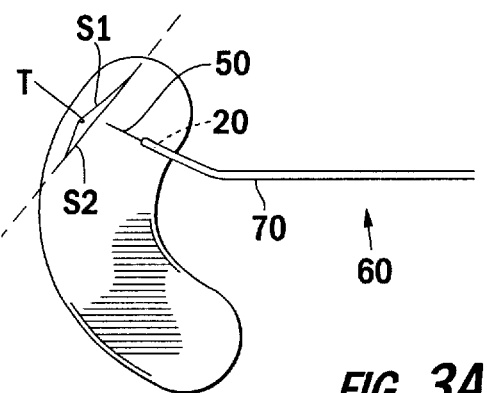
FIGS. 3A–3D illustrates the method for repairing a knee meniscal tear.

A description of the preferred embodiments of the present invention will now be presented with reference to FIGS. 1–3D.

The preferred exemplary embodiment of the present invention comprises a fastener, driving device, and method for repairing a soft-tissue tear in a patient. The system 10 of the present invention comprises a fastener 20 and an elongated driving device 60.

In a preferred embodiment shown in FIGS. 1 and 2, the fastener 20 has a root portion 21 that has a proximal end 22, a distal end 23, and a length 24. The root portion 21 further has a distal section 25 tapering toward the distal end 23, in this specific embodiment the distal section 25 generally forming a cone. Alternatively, a self-tapping distal section could be implemented. In use an insertion of fastener 20 into soft tissue is facilitated by the conical-shaped distal section 25. The proximal section 30 of the root portion 21 has a substantially constant radius.

Atop the root portion 21 a helical protrusion (i.e., a thread) 26 proceeds along a central section 27 between the proximal end 22 and the distal end 23. A short section adjacent the distal end 23 is substantially smooth and does not have a helical protrusion thereon. The protrusion 26 has a helical pitch along the central section 27, with a substantially constant value 28 along the distal section 25 proximal of the distal end 23. Extending proximal of the distal section 25, along a proximal section 30, the helical protrusion 26 has a variable value 31, decreasing in a proximal direction to the proximal end 22. In use the decrease in helical pitch along the proximal section 30 serves to bring two sides S1,S2 of a tear T into apposition as the fastener 20 is advanced across the two sides S1,S2 of the tear T in a screwing motion.

Preferably the helical protrusion 26 has a buttress form for resisting an axial force from pulling the fastener out of the tear and from pulling the two sides of the tear apart. The "buttress form," is a term known in the art of tool making, and is known to have advantages in applications involving high stresses along the longitudinal (helical) axis in one direction. The "pressure flank," the face of the protrusion taking the thrust, is generally desired to be nearly perpendicular to the helical axis so that the radial component of the thrust is reduced to a minimum.

In fastener 20 the helical protrusion 26 further has a leading face 32 facing the distal end 23. The leading face 32 makes a first angle 33 with a helical axis vector 34 having a directionality pointing from the proximal 22 to the distal end 23. The leading face 32 adjacent the proximal end 22 serves to resist an axial force in the direction of the helical axis vector 34.

In fastener 20 the helical protrusion 26 further has a trailing face 36 facing the proximal end 22. The trailing face 36 makes a second angle 37 with the helical axis vector 34. The trailing face 36 adjacent the distal end 23 serves to resist an axial force in a direction opposite the direction of the helical axis vector 34.

The helical protrusion 26 also has a radial depth measured from the surface of the root portion 21 to the crest of the helical protrusion 26. The thread depth 40 along the proximal section 30 has a substantially constant value. The thread depth 42 along the distal section 29 decreases from the value 40 along the proximal section 30 to a minimum value at the distal end 43 of the helical protrusion 26.

The fastener material in the preferred embodiment comprises a biodegradable plastic biocompatible with the soft tissue of the patient. Exemplary materials include a nontoxic blend of polycaprolactone and polyglycolide, a blend of polylactide and polyglycolide, pure polydioxanone, poly(ethylene oxide):poly(butylene terephthalate), polyorthoester, polyhydroxybutyrate, or cross-linked collagen. The material is designed to be sufficiently flexible and strong to withstand natural knee movement during healing. The material is also designed to be biodegradable within a first time span greater than or equal to a second time span over which the sides S1,S2 of the tear T can knit together. In other words, the material is resorbed over a time span commensurate with the healing process, so that, once the tear T is healed, the fastener 20 can gradually degrade, leaving a healed meniscus with no foreign material embedded therein.

In the preferred embodiment, fastener 20 further has an axial bore 44 therethrough generally along the helical axis 34. In an alternate embodiment, the bore 44 may not extend completely through to the distal end 23. In the embodiment illustrated herein, bore 44 proceeds from proximal end 22 to distal end 23, and has a noncircular cross-sectional shape to permit an elongated driving device having a noncircular cross-sectional shape to pass into bore 44 and to advance fastener 20 into the meniscus M by being rotated in a direction having a handedness commensurate with the helically shaped protrusion 26 (see FIG. 3C). The cross-sectional shape 45 of the bore, as shown in FIG. 2, is triangular, although this is not intended as a limitation, as other noncircular bores may be contemplated by one of skill in the art.

The fastener 20 further has a head 46 affixed the root's proximal end 22, the bore 44 extending therethrough as well. The head 46 has a diameter 47 at least as great as a maximum diameter 48 of the helical protrusion 26 and a substantially smooth periphery 49.

The driving device of a preferred embodiment comprises an elongated driving device 60 comprising a needle 50 inserted through an elongated tubular member 70.

Figure 3B:
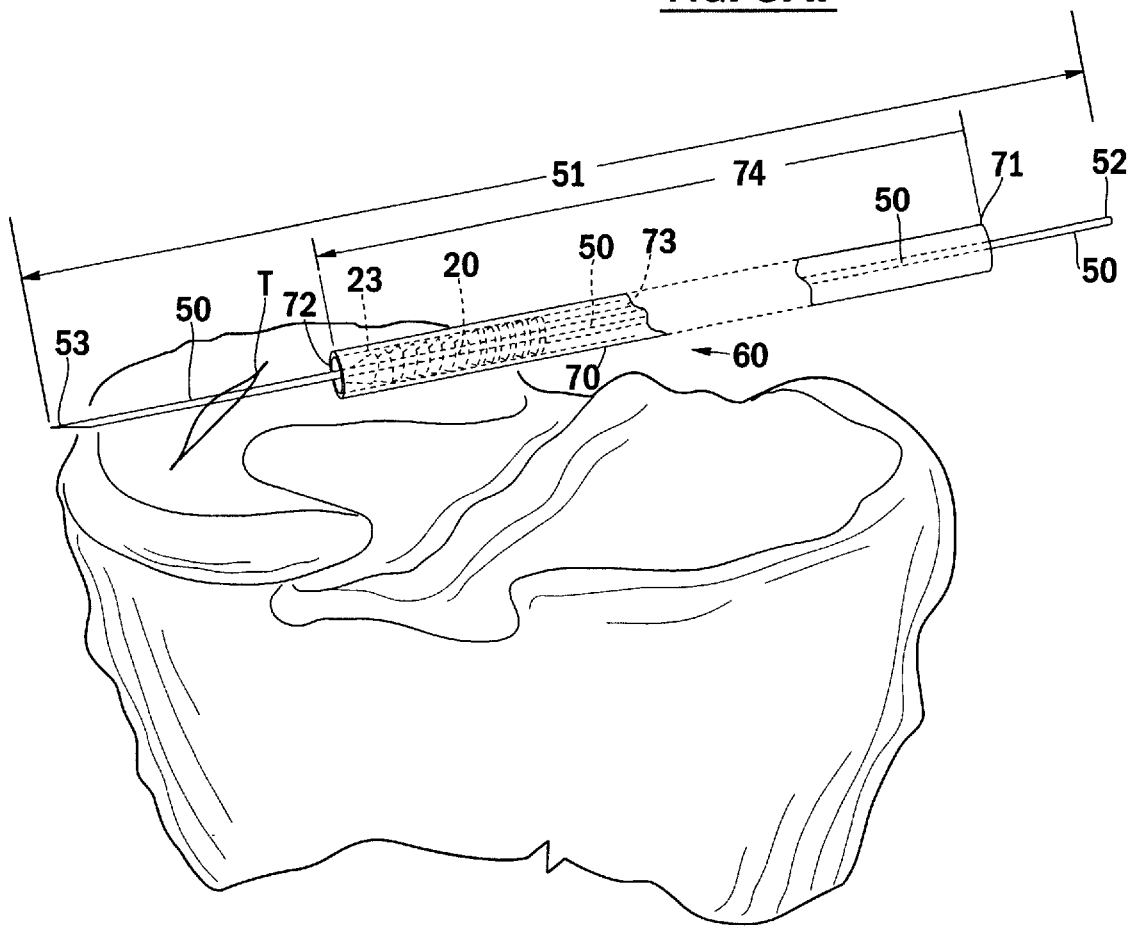
Figure 3C:
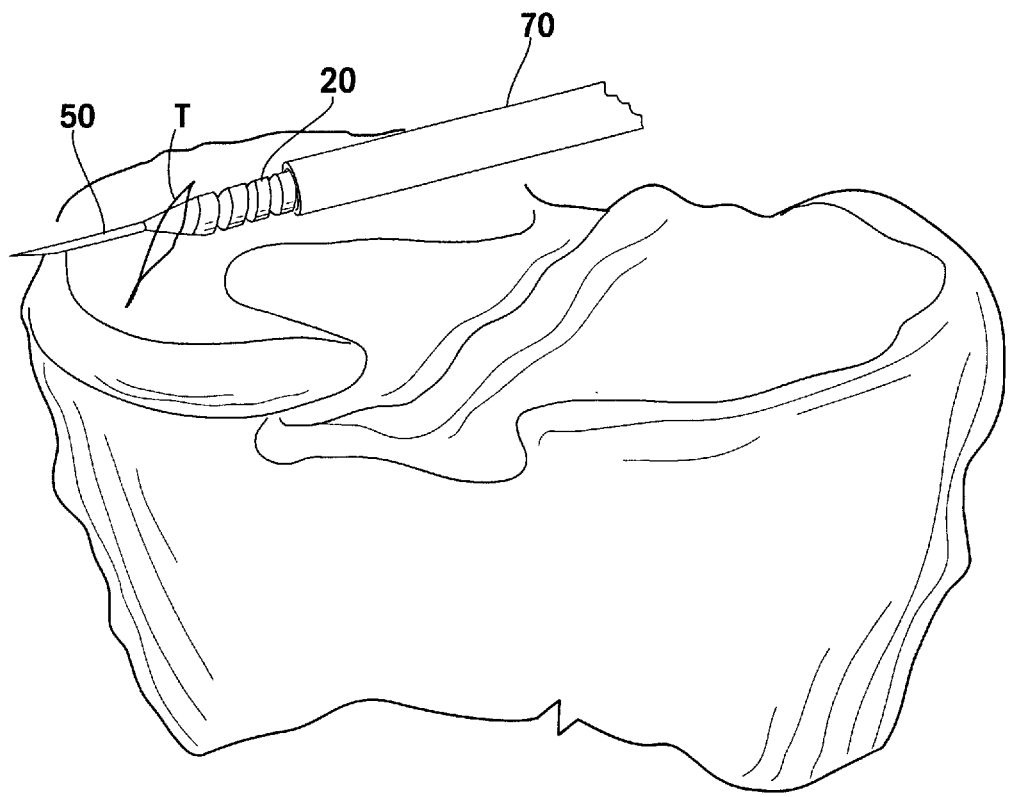

The needle 50 has a length 51, a proximal end 52, and a pointed distal tip 53 (see FIG. 3B). Needle 50 further has a cross-sectional triangular shape along at least a distal section dimensioned axially to be slidable through the bore 44 of the fastener 20 and rotationally to drive the fastener 20 (FIG. 3C).

In use needle 50 is axially movable distalward to a first position wherein the needle tip 53 protrudes from distal end 23 of fastener 20 (FIG. 3A). In this position, needle tip 53 can pierce the tissue to be repaired (FIG. 3B), aiding in advancing fastener 20, preparatory to rotating needle 50 and hence fastener 20, which are rotationally coupled.

A further component of system 10 comprises a cannula member 70 for protecting fastener 20 during insertion into the soft tissue area adjacent the tear T (see FIGS. 3A–3D). Cannula member 70 has a proximal end 71 and a distal end 72. In addition, cannula member 70 has an axial bore 73 therethrough from distal end 72 to proximal end 71. Bore 73 is dimensioned to permit the fastener 20 and the needle 50 to fit therein and to permit sliding and rotational movement therebetween.

Cannula member 70 has a length 74 shorter than needle length 51 permitting distal tip 53 and proximal end 52 of needle 50 to protrude from distal end 72 and proximal end 71, respectively, of the cannula member 70.

In the embodiment contemplated for repairing a knee meniscus, the needle, the tubular member, and the cannula member all similarly have a curve therein for enabling an operator to manipulate the system into a position to approach a soft tissue tear around a curved radius. In the preferred embodiment, this curve comprises a 10–30 degree generally upward bend.

The method of the present invention for repairing a tear T in soft tissue of a patient, shown in FIGS. 3A–3D for repairing a meniscal tear, comprises the steps of moving the needle 42 axially through the bore 44 of the fastener 20, the distal tip 53 of the needle 50 emerging from the distal end 23 of the fastener 20 (FIG. 3A). The needle tip 53 then pierces the tear T, and the needle 50 is advanced across both sides S1,S2 (FIG. 3B).

The fastener 20 is inserted over the needle 50 into an area of soft tissue adjacent the tear T. The operator then manipulates the distal end 23 of the fastener 20 to a position generally normal to the long axis of the tear T (FIG. 3C).

Figure 3D:
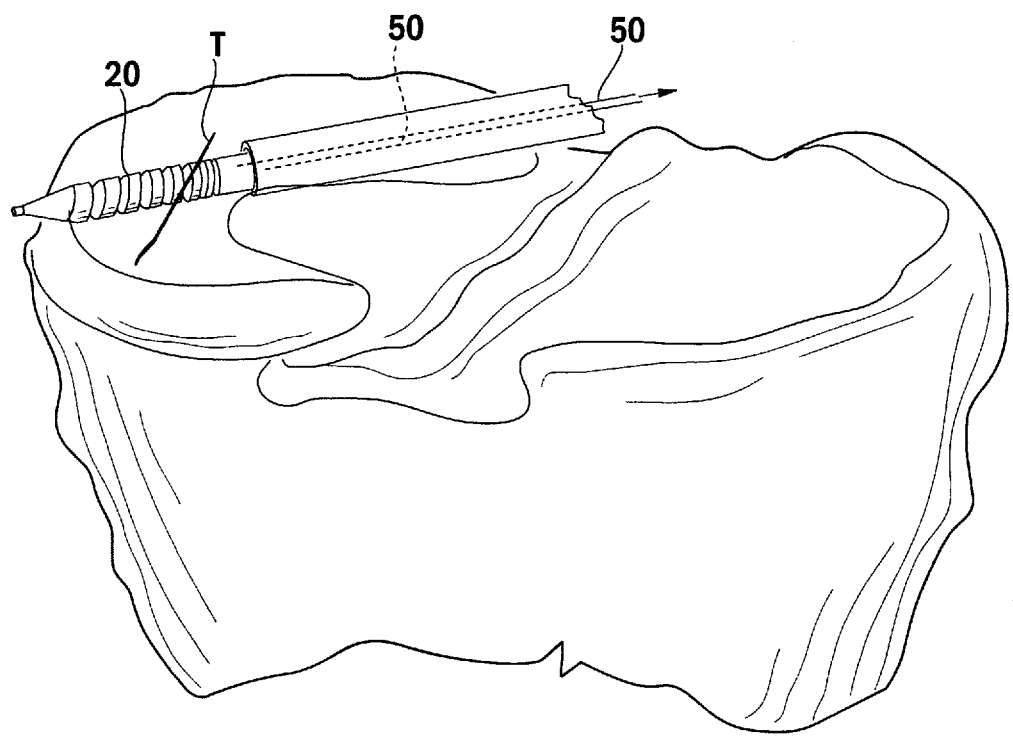

The next step comprises driving the fastener 20 across the tear T in a screwing motion (FIG. 3C), the decrease in the helical pitch 31 serving to bring two sides of the tear S1,S2 into apposition as the fastener 20 is advanced (FIG. 3D). Given the rotationally coupled needle 50 and fastener 20, the driving step comprises rotating the needle 50 and hence the fastener 20. Since the needle 50 and fastener 20 are axially slidable relative to each other, the needle 50 can then be removed from the fastener 20 and all instruments removed from the surgical site once the sides of the tear have been drawn together (FIG. 3D).

It may be appreciated by one skilled in the art that additional embodiments may be contemplated, including fasteners, systems, and methods for repairing other soft tissue tears, such as in the shoulder.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and method illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A fastener for repairing a tear in soft tissue of a patient, the fastener having:

a root portion having a proximal end, a distal end, and a distal section having a narrowing cross section toward the distal end; and a helical protrusion atop the root portion along a central section thereof between the proximal end and the distal end, the helical protrusion having a helical pitch along the central section, the helical pitch having a substantially constant value along a distal section extending proximal of the distal end and having a variable value extending proximal of the distal section, wherein the helical pitch decreases from the distal end to the proximal end, and wherein the helical protrusion has a radial depth from an outer edge to the root portion, the radial depth smaller adjacent the distal end than along the variable section.

2. The fastener recited in claim 1, further having an axial bore at least partially therethrough generally along a helical axis vector proceeding from the head and into the root portion from the proximal end, the bore having a noncircular cross-sectional shape.

3. The fastener recited in claim 2, wherein the axial bore extends through to the root distal end.

4. The fastener recited in claim 2, wherein the cross-sectional shape of the axial bore is substantially triangular.

5. The fastener recited in claim 1, further having a head affixed to the root proximal end having a diameter at least as great as a maximum diameter of the helical protrusion, the head having a substantially smooth periphery.

6. The fastener recited in claim 1, wherein the helical protrusion further has a leading face facing the distal end, the leading face making a first angle with a helical axis vector having a directionality pointing from the proximal to the distal end, the first angle decreasing from a first oblique angle adjacent the distal end to a second oblique angle adjacent the proximal end, the second oblique angle smaller than the first oblique angle.

7. The fastener recited in claim 6, wherein the helical protrusion further has a trailing face facing the proximal end, the trailing face making a second angle with the helical axis vector, the second angle decreasing from a first acute angle adjacent the distal end to a second acute angle adjacent the proximal end, the second acute angle smaller than the first acute angle.

8. The fastener recited in claim 1, wherein the fastener material comprises a biodegradable plastic biocompatible with the soft tissue of the patient and further biodegradable within a first time span greater than or equal to a second time span over which the sides of the tear can knit together.

9. The fastener recited in claim 1, wherein the root portion has a substantially constant radius from the proximal end to the distal section.

10. The fastener recited in claim 1, wherein the root portion distal section has a generally conical shape.

11. A system for repairing a tear in soft tissue of a patient, the system comprising:

a fastener having:

a root portion having a proximal end, a distal end, and a distal section having a narrowing cross section toward the distal end;

a helical protrusion atop the root portion along a central section thereof between the proximal end and the distal end, the helical protrusion having a helical pitch along the central section, the helical pitch having a substantially constant value along a distal section extending proximal of the distal end and having a variable section extending proximal of the distal section, wherein the helical pitch decreases from the distal end to the proximal end, and wherein the helical protrusion has a radial depth from an outer edge to the root portion, the radial depth smaller adjacent the distal end than along the variable section; and an axial bore at least partially therethrough generally along a helical axis vector proceeding from the head and into the root portion from the proximal end, the bore having a noncircular cross-sectional shape; and an elongated driving device having:
    a distal end having means for mating with the fastener bore;
    a proximal end having means for being rotationally driven; and
    a noncircular cross-sectional shape along a distal section adjacent the distal end, the distal section dimensioned for entry into the bore and to permit relative axial sliding and rotational coupling movement therebetween.

12. The system recited in claim 11, wherein the fastener further has a head affixed to the root proximal end having a diameter at least as great as a maximum diameter of the helical protrusion, the head having a substantially smooth periphery.

13. The system recited in claim 11, wherein the driving device comprises a needle having a pointed distal tip.

14. A method for repairing a soft-tissue tear, the method comprising the steps of:

moving a needle axially into a bore of the fastener, the needle adapted to drive the fastener, the fastener having:
    a root portion having a proximal end, a distal end, and a distal section having a narrowing cross section toward the distal end; and
    a helical protrusion atop the root portion along a central section thereof between the proximal end and the distal end, the helical protrusion having a helical pitch along the central section, the helical pitch having a substantially constant value along a distal section extending proximal of the distal end and having a variable section extending proximal of the distal section, wherein the helical pitch decreases from the distal end to the proximal end, and wherein the helical protrusion has a radial depth from an outer edge to the root portion, the radial depth smaller adjacent the distal end than along the variable section;

inserting the fastener into an area of soft tissue adjacent the tear;

manipulating the distal end of the fastener to a position generally normal to a long axis of the tear;

piercing the tissue to be repaired with a tip of the needle;

driving the fastener across the tear in a screwing motion by rotating the needle and hence the fastener, the proximal decrease in the helical pitch serving to bring two sides of the tear into apposition as the fastener is advanced.

\* \* \* \* \*